(12) United States Patent
Gofman (10) Patent No.: US 12,431,727 B2
(45) Date of Patent: *Sep. 30, 2025

(54) AUTOMATIC ACTIVATION OF CONTINUOUS GLUCOSE MONITORING (CGM) TRANSMITTER

(71) Applicant: Ascensia Diabetes Care Holdings AG, Basel (CH)

(72) Inventor: Igor Y. Gofman, Croton-on-Hudson, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 90 days.

This patent is subject to a terminal disclaimer.

(21) Appl. No.: 18/310,814

(22) Filed: May 2, 2023

(65) Prior Publication Data

US 2023/0268751 A1 Aug. 24, 2023

Related U.S. Application Data

(63) Continuation of application No. 17/024,635, filed on Sep. 17, 2020, now Pat. No. 11,677,254.
(Continued)

(51) Int. Cl.
*H02J 7/00* (2006.01)
*A61B 5/00* (2006.01)
(Continued)

(52) U.S. Cl.
CPC .......... *H02J 7/0063* (2013.01); *A61B 5/0002* (2013.01); *A61B 5/14532* (2013.01);
(Continued)

(58) Field of Classification Search
CPC ... A61B 5/0002; A61B 5/14532; A61B 5/002; A61B 5/7225; A61B 2560/0204;
(Continued)

(56) References Cited

U.S. PATENT DOCUMENTS

2009/0076336 A1 3/2009 Mazar et al.
2011/0315564 A1 12/2011 Guthrie et al.
(Continued)

FOREIGN PATENT DOCUMENTS

CN 108078570 A 5/2018
CN 110177501 A 8/2019
(Continued)

OTHER PUBLICATIONS

Japanese Patent Application 2022-517492 Notice of Allowance issued Jun. 4, 2024.
(Continued)

*Primary Examiner* — Chu Chuan Liu
(74) *Attorney, Agent, or Firm* — Erise IP, P.A.

(57) ABSTRACT

A battery-operated electronic device, such as, e.g., a continuous glucose monitoring (CGM) transmitter, has a switch disconnect circuit that reduces battery discharge while the device is stored and/or in "shelf mode." The device has two externally-accessible activation pads each configured to contact a same electrical conductor positioned in packaging for the device that causes the switch disconnect circuit to disconnect the battery from device electronics while the device is in the packaging. Upon removal of the device from the packaging, the two activation pads no longer contact the electrical conductor, causing the switch disconnect circuit to automatically connect the battery to the device electronics. Methods of reducing battery discharge in a battery-operated electronic device and other aspects are also described.

20 Claims, 6 Drawing Sheets

Related U.S. Application Data (60) Provisional application No. 62/901,976, filed on Sep. 18, 2019.

(51) Int. Cl.
*A61B 5/145* (2006.01)
*H01M 10/44* (2006.01)
*H01M 50/572* (2021.01)

(52) U.S. Cl.
CPC ....... *H01M 10/448* (2013.01); *H01M 50/572* (2021.01); *A61B 2560/0209* (2013.01); *A61B 2560/0214* (2013.01); *A61B 2562/242* (2013.01); *H01M 2220/30* (2013.01)

(58) Field of Classification Search
CPC .... A61B 2560/0209; A61B 2560/0214; A61B 2562/242; H01M 10/448; H02J 7/0032; H02J 7/0063
See application file for complete search history.

(56) References Cited

U.S. PATENT DOCUMENTS

| | | |
|---|---|---|
| 2015/0018643 A1 | 1/2015 | Cole et al. |
| 2017/0172472 A1 | 6/2017 | Wedekind et al. |
| 2017/0172473 A1* | 6/2017 | Wedekind ........... A61B 5/14503 |
| 2018/0000563 A1* | 1/2018 | Shanjani ............... A61B 5/0015 |
| 2018/0027106 A1 | 1/2018 | Mandapaka et al. |
| 2019/0081493 A1 | 3/2019 | Thiel et al. |
| 2019/0142315 A1* | 5/2019 | Love .................... A61B 5/6833 |
| | | 600/316 |

FOREIGN PATENT DOCUMENTS

| | | |
|---|---|---|
| CN | 110177502 A | 8/2019 |
| JP | H0981118 A | 3/1997 |
| JP | 2003530135 A | 10/2003 |
| JP | 2006074922 A | 3/2006 |
| JP | 2006516100 A | 6/2006 |
| JP | 2006254650 A | 9/2006 |
| JP | 2009297166 A | 12/2009 |
| JP | 2016005585 A | 1/2016 |
| JP | 2016520379 A | 7/2016 |
| TW | 201900230 A | 1/2019 |
| WO | 2018125841 A1 | 7/2018 |

OTHER PUBLICATIONS

Taiwan Patent Application 109131992 Notice of Allowance issued May 23, 2024.
Taiwan Patent Application 113130287, Office Action, issued Dec. 19, 2024.
Taiwan Patent Application 109131992 Official Letter issued Jan. 12, 2024.
Chinese Patent Application 202080065690.2, First Office Action, issued Feb. 18, 2025.
Japanese Patent Application 2024-107006 Office Action issued Apr. 22, 2025.
Chinese Patent Application 202080065690.2, Notification to Grant Patent Right, issued Jul. 31, 2025.

* cited by examiner

AUTOMATIC ACTIVATION OF CONTINUOUS GLUCOSE MONITORING (CGM) TRANSMITTER

RELATED APPLICATION

This patent application is a continuation application claiming priority benefit, with regard to all common subject matter, of U.S. patent application Ser. No. 17/024,635, filed Sep. 17, 2020, and entitled "AUTOMATIC ACTIVATION OF CONTINUOUS GLUCOSE MONITORING (CGM) TRANSMITTER" ("the '635 Application"). The '635 Application claims priority to and the benefit of U.S. Provisional Patent Application No. 62/901,976, filed Sep. 18, 2019, and entitled "AUTOMATIC ACTIVATION OF CONTINUOUS GLUCOSE MONITORING (CGM) TRANSMITTER." The identified earlier-filed patent applications are hereby incorporated by reference in their entirety into the present application.

FIELD

This disclosure relates to wireless transmitters for continuous glucose monitoring systems.

BACKGROUND

Continuous analyte sensing in an in-vivo and/or in-vitro sample, such as continuous glucose monitoring (CGM), has become a routine sensing operation, particularly in diabetes care. By providing real-time glucose concentrations, therapeutic/clinical actions may be applied more timely and the glycemic condition may be better controlled.

During a CGM operation, a biosensor is typically inserted subcutaneously and is continuously operated in an environment surrounded by tissue and interstitial fluid. The biosensor inserted under the skin provides a signal to a wireless CGM transmitter of the CGM sensor apparatus, and that signal is indicative of the user's blood glucose level. These measurements may be made automatically many times throughout the day (e.g., every few minutes or at some other interval).

The wireless CGM transmitter is typically adhered to the outer surface of a user's skin, such as on the abdomen, or the back of the upper arm, while the biosensor is inserted through the skin so as to contact interstitial fluid.

The wireless CGM transmitter is usually a battery-operated device that may first be stored and/or sit on a store or warehouse shelf ("shelf mode") for an extended period of time before a user begins using it. Although some conventional CGM transmitters may be packaged in a low power mode, significant battery discharge during storage or shelf mode may still occur. Other conventional CGM transmitters may have an electromechanical activation switch that is initially set such that the battery is disconnected from the CGM electronics in order to save battery power during storage or shelf mode. Such a switch, however, disadvantageously adds bulk and cost to the CGM transmitter in view of the switch's size and need to be sealed. Furthermore, such conventional CGM transmitters rely on the user to activate the transmitter by resetting the activation switch in order to connect the battery to the CGM electronics.

Accordingly, improved wireless CGM transmitters and methods of reducing battery discharge while in storage and/or shelf mode and of activating the CGM transmitter are desired.

SUMMARY

According to a first aspect, a method of reducing battery discharge in a wireless continuous glucose monitoring (CGM) transmitter includes receiving the CGM transmitter in a package configured to receive and enclose the CGM transmitter therein, electrically disconnecting a battery of the CGM transmitter from transmitter electronics of the CGM transmitter automatically in response to the CGM transmitter being received in the package, and electrically connecting the battery to the transmitter electronics automatically in response to the CGM transmitter being removed from the package.

According to a second aspect, a wireless continuous glucose monitoring (CGM) transmitter includes first and second activation pads, transmitter electronics, and a battery having a positive terminal and a negative terminal wherein the negative terminal is coupled to the first activation pad. The CGM transmitter also includes a switch disconnect circuit having an input pin, an output pin, and an enable pin, wherein the input pin is coupled to the positive terminal of the battery, the output pin is coupled to a power input of the transmitter electronics, and the enable pin is coupled to the second activation pad. The switch disconnect circuit is configured to electrically disconnect the battery from the transmitter electronics in response to an electrical connection of the first activation pad to the second activation pad.

According to a third aspect, a method of reducing battery discharge in a wireless continuous glucose monitoring (CGM) transmitter includes coupling an input of a switch disconnect circuit to a positive terminal of a battery and coupling an output of the switch disconnect circuit to a power input of transmitter electronics of the CGM transmitter. The method also includes coupling a first activation pad to a negative terminal of the battery, and coupling a second activation pad to an enable pin of the switch disconnect circuit. The method further includes packaging the CGM transmitter in a package comprising an electrical conductor positioned to contact both the first and second activation pads, causing the switch disconnect circuit to disconnect the battery from the transmitter electronics.

According to a fourth aspect, a battery-operated electronic device includes first and second activation pads, device electronics, and a battery having a positive terminal and a negative terminal, wherein the negative terminal is coupled to the first activation pad. The battery-operated electronic device also includes a switch disconnect circuit having an input pin, an output pin, and an enable pin, wherein the input pin is coupled to the positive terminal of the battery, the output pin is coupled to a power input of the device electronics, and the enable pin is coupled to the second activation pad. The switch disconnect circuit is configured to electrically disconnect the battery from the device electronics in response to an electrical connection of the first activation pad to the second activation pad.

Still other aspects, features, and advantages of this disclosure may be readily apparent from the following description and illustration of a number of example embodiments and implementations, including the best mode contemplated for carrying out the invention. This disclosure may also be capable of other and different embodiments, and its several details may be modified in various respects, all without departing from the scope of the invention. For example, some embodiments of this disclosure may be applicable to other battery-operated electronic devices that are provided to a user with a battery included. Such battery-operated electronic devices may include various game, music, video, communication, and/or computer devices, and/or combinations thereof. This disclosure is intended to cover all modifications, equivalents, and alternatives falling within the scope of the appended claims (see further below).

BRIEF DESCRIPTION OF THE DRAWINGS

The drawings, described below, are for illustrative purposes and are not necessarily drawn to scale. Accordingly, the drawings and descriptions are to be regarded as illustrative in nature, and not as restrictive. The drawings are not intended to limit the scope of the invention in any way.

DETAILED DESCRIPTION

Battery-operated electronic devices that include one or more batteries may sit on a store or warehouse shelf for many months before use (which can be referred to as "shelf mode") These electronic devices, even those initially set in a low power mode, may be subject to significant battery discharge while in shelf mode. In one or more embodiments described herein, a battery-operated electronic device, which may be, e.g., a wireless continuous glucose monitoring (CGM) transmitter, may include a switch disconnect circuit that together with packaging configured to receive and enclose the device therein significantly reduces battery discharge while the device is stored and/or in shelf mode. Furthermore, battery-operated electronic devices in accordance with one or more embodiments described herein may automatically activate upon removal of the device from its packaging.

These and other features of inventive battery-operated electronic devices in accordance with one or more embodiments will be described below in connection with wireless CGM transmitters and FIGS. 1-6.

Some conventional battery-operated CGM transmitters are initially set and packaged in a low power mode. These CGM transmitters, however, may still consume battery power. For example, a microcontroller of a CGM transmitter in a typical low power mode may still consume 1-2 μA. After 12 months of storage or shelf mode, the battery may lose about 9-18 mAh. This represents enough battery power to operate a CGM transmitter for almost two weeks. Manufacturers typically address this battery discharge problem by providing a larger, more expensive battery with sufficient power to compensate for extended periods of storage and/or shelf mode.

Other conventional battery-operated CGM transmitters may be manufactured without an internal connection between the battery and transmitter electronics, having instead two externally-accessible conductive pads, one connected to the battery and the other connected to the power input of the transmitter electronics. Upon attachment to a CGM sensor assembly that may be positioned on a user's skin, an electrical connector on the CGM sensor assembly may contact the two conductive pads, electrically connecting the battery to the transmitter electronics. This type of electrical connection, however, has the disadvantage of not being reliable enough for a wearable device, which is subject to vibrations caused by a user's movement. If the electrical connection between the two conductive pads becomes open (i.e., one or both of the two conductive pads loses contact with the CGM sensor assembly electrical connector), even for a few milliseconds, the CGM transmitter can lose data and may require additional recalibration upon restoration of power.

Figure 1:
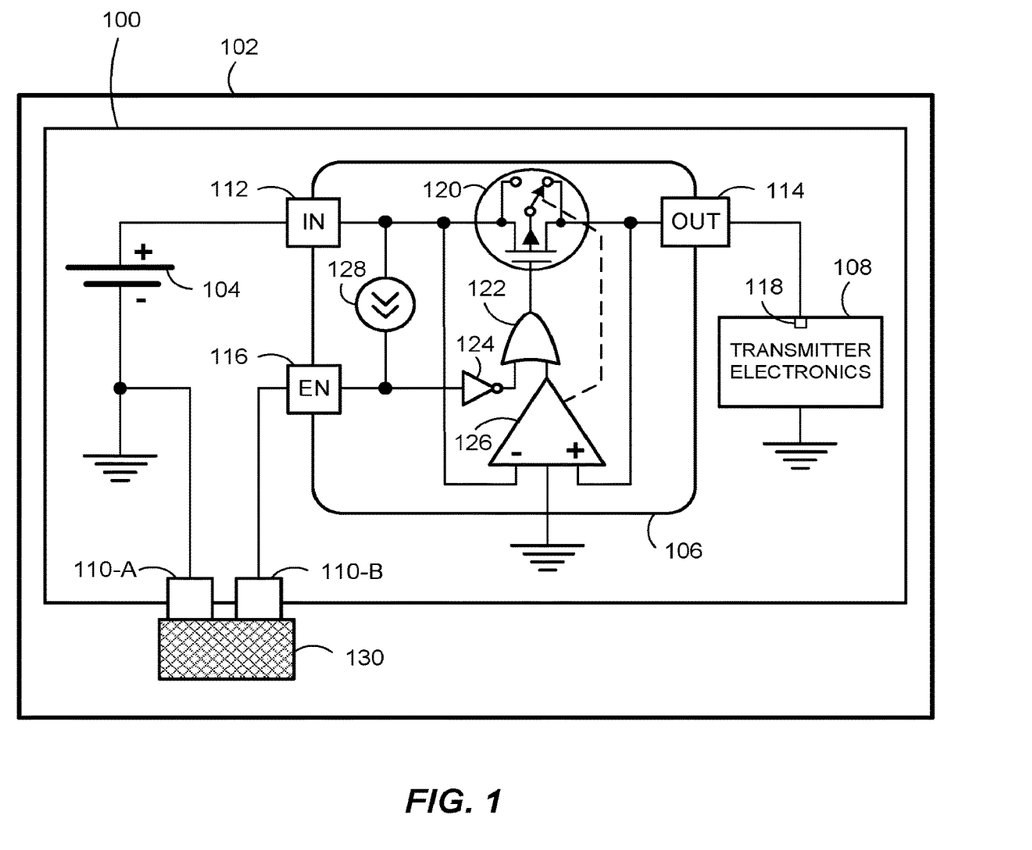
FIG. 1 illustrates a schematic diagram of a wireless continuous glucose monitoring (CGM) transmitter received in a CGM transmitter package according to one or more embodiments.

FIG. 1 illustrates a wireless CGM transmitter 100 and a CGM package 102 configured to receive CGM transmitter 100 therein in accordance with one or more embodiments. CGM transmitter 100 advantageously reduces battery discharge during storage and/or shelf mode while packaged in CGM package 102 and automatically activates upon removal from CGM package 102. Advantageously, once removed from CGM package 102, CGM transmitter 100 does not require any electrical connection by any external device, connector, or component, and does not require any other action by a user in order to be powered by its battery.

CGM transmitter 100 may provide Bluetooth, WiFi, RF, or other suitable wireless communications. CGM transmitter 100 may include at least one battery 104, a switch disconnect circuit 106, transmitter electronics 108, a first activation pad 110-A, and a second activation pad 110-B. Battery 104 may have a positive ("+") terminal and a negative ("−") terminal. The negative ("−") terminal of battery 104 may be coupled to first activation pad 110-A. Switch disconnect circuit 106 may have an input pin 112, an output pin 114, and an enable pin 116, wherein input pin 112 may be coupled to the positive ("+") terminal of battery 104, output pin 114 may be coupled to a power input 118 of transmitter electronics 108, and enable pin 116 may be coupled to second activation pad 110-B.

Switch disconnect circuit 106 may also include a transistor switch 120, a logic gate 122, an inverter 124, a differential amplifier 126 (acting as a comparator), and a current source 128. Transistor switch 120 may be coupled in series (i.e., in the direction of current flow through transistor switch 120 when turned ON) between input pin 112 and the output pin 114. Logic gate 122 may have first and second inputs and an output, wherein the output may be coupled to the control input of transistor switch 120 to control the ON/OFF operation of transistor switch 120. In some embodiments, transistor switch 120 may include a MOSFET and, more particularly, may be a P-channel MOSFET wherein its drain is coupled to input pin 112, its source is coupled to output pin 114, and its gate is coupled to the output of logic gate 122. In the embodiments including the P-channel MOSFET, logic gate 122 may include an OR gate. Other types of transistor switches and logic gates alternatively may be used. Inverter 124 may be coupled between enable pin 116 and the first input of logic gate 122. Differential amplifier 126 may have an inverting input coupled to input pin 112, a non-inverting input coupled to output pin 114, and an output coupled to the second input of logic gate 122. Current source 128 may be coupled between input pin 112 and enable pin 116. In some embodiments, switch disconnect circuit 106 may include a nanopower ideal diode, such as, e.g., a MAX40203 Ideal Diode by Maxim Integrated, of San Jose, California.

Switch disconnect circuit 106 may operate as follows: with second activation pad 110-B electrically floating (i.e., second activation pad 110-B is not electrically connected to first activation pad 110-A, ground, or voltage), enable pin 116 is also electrically floating. Current source 128, which in some embodiments may provide about 14-16 nA in response thereto, enables switch disconnect circuit 106. That is, inverter 124 outputs a logical LOW signal to logic (OR) gate 122. Logic (OR) gate 122 also receives a logical LOW signal from the output of differential amplifier 126, causing logic (OR) gate 122 to output a logical LOW signal to transistor (P-channel MOSFET) switch 120. The logical LOW signal received at the control input (gate) of transistor (P-channel MOSFET) switch 120 causes it to turn ON, creating a current path between input pin 112 and output pin 114. This connects battery 104 to power input 118 of transmitter electronics 108. In this enable mode, the voltage drop across transistor (P-channel MOSFET) switch 120 may be less than 20 mV, in some embodiments.

Upon electrical connection of second activation pad 110-B to, e.g., first activation pad 110-A, which is connected to ground (i.e., the negative ("−") battery terminal), enable pin 116 is also grounded, which disables switch disconnect circuit 106. That is, inverter 124 outputs a logical HIGH signal to logic (OR) gate 122, which continues to receive a logical LOW signal from the output of differential amplifier 126. Logic (OR) gate 122 responds by outputting a logical HIGH signal to the control input (gate) of transistor (P-channel MOSFET) switch 120, which causes transistor (P-channel MOSFET) switch 120 to turn OFF. Transistor (P-channel MOSFET) switch 120 is thus open (i.e., no current path exists between input pin 112 and output pin 114), which disconnects battery 104 from power input 118 of transmitter electronics 108.

In this disable mode, the quiescent current may be about 130 nA in some embodiments. During, e.g., a 12 month storage and/or shelf mode of CGM transmitter 100, battery 104 may discharge while in this disable mode by only about 1.1 mAh (i.e., 130 nA×24 hours×365 days). This reduced battery discharge rate is advantageously comparable to a typical self-discharge rate of a LiMn battery.

To implement the disable mode while CGM transmitter 100 is in storage and/or shelf mode, CGM package 102 may be provided (e.g., by a CGM transmitter manufacturer or package provider), which is configured to receive and enclose CGM transmitter 100 therein. CGM package 102 includes an electrical conductor 130 positioned such that first activation pad 110-A and second activation pad 110-B, which are each externally-accessible on an outside surface of CGM transmitter 100, both come into electrical contact with electrical conductor 130 upon CGM transmitter 100 being received and enclosed within CGM package 102, as shown in FIG. 1. Electrically connecting first activation pad 110-A to second activation pad 110-B via electrical conductor 130 grounds enable pin 116, which disables switch disconnect circuit 106 as described above. Electrical conductor 130 may be, e.g., a metal plate or conductive carbonized rubber, and may be positioned inside of and attached to and/or seated within CGM package 102 in any conventional manner (e.g., via an adhesive or fastener or fitted within a molded insert received in CGM package 102, etc.). Other conductive materials may be used for electrical conductor 130.

FIGS. 2A-2D illustrate a CGM transmitter 200, which may be identical or substantially similar to CGM transmitter 100, that may have a first activation pad 210-A and a second activation pad 210-B externally-accessible on a bottom surface 211 of CGM transmitter 200 in accordance with one or more embodiments. First activation pad 210-A and second activation pad 210-B may be coupled within CGM transmitter 200 to operate as described above for first activation pad 110-A and second activation pad 110-B of CGM transmitter 100 with respect to connection and disconnection of one or more batteries to and from transmitter electronics of CGM transmitter 200.

Figure 2A:
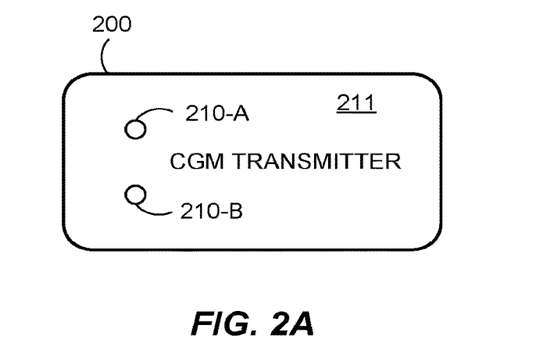
FIG. 2A illustrates a bottom view of a CGM transmitter according to one or more embodiments.
Figure 2B:
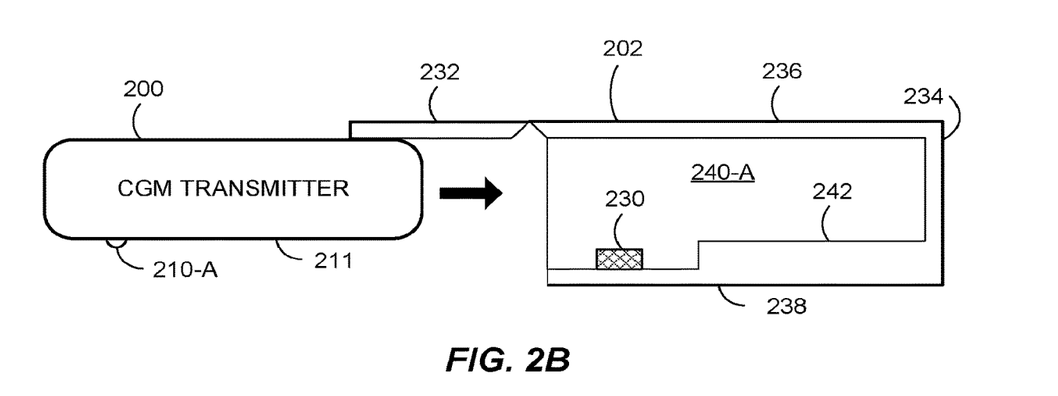
FIG. 2B illustrates a side view of the CGM transmitter of FIG. 2A and a CGM transmitter package (with a side panel removed) according to one or more embodiments.
Figure 2C:
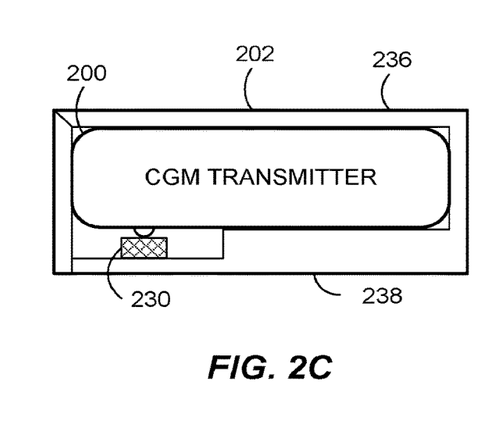
FIG. 2C illustrates a side view of the CGM transmitter received in the CGM transmitter package of FIG. 2B (with the side panel removed) according to one or more embodiments.
Figure 2D:
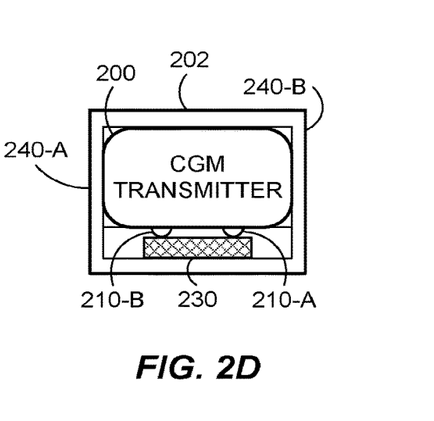
FIG. 2D illustrates a front view of the CGM transmitter received in the CGM transmitter package of FIG. 2C (with the front panel removed) according to one or more embodiments.

FIGS. 2B-2D illustrate a CGM package 202, which may be identical or substantially similar to CGM package 102, and may be configured to receive and enclose therein CGM transmitter 200 in accordance with one or more embodiments.

As shown in FIGS. 2B-2D, CGM package 202 may be a generally square or rectangular package or box-like structure of conventional paper board construction having a front panel 232, a back panel 234, a top panel 236, a bottom panel 238, and two side panels 240-A and 240-B. CGM package 202 may also include an electrical conductor 230 attached to and/or positioned or seated within the interior of CGM package 202 such that electrical conductor 230 electrically contacts both first activation pad 210-A and second activation pad 210-B upon receipt of CGM transmitter 200 in CGM package 202. Electrical conductor 230 may be, e.g., a metal plate, a strip of conductive carbonized rubber, or any other suitable electrical conductor. Electrical conductor 230 may be attached to an interior surface (such as, e.g., an interior surface of bottom panel 238) or interior structure of CGM package 202 in any suitable manner (e.g., via an adhesive or fastener). CGM package 202 may further include a support surface 242 configured to receive thereon a portion of CGM transmitter 200. Support surface 242 may be of the same paper board construction as the panels of CGM package 202 or, alternatively, may be, e.g., a molded and/or bottom insert configured to be received in CGM package 202 prior to CGM transmitter 200. Other types or constructions of support surface 242 are possible. CGM package 202 may be configured and constructed, e.g., with one or more support surfaces 242 and/or guide structures, such that CGM transmitter 200 can be guided and received in CGM package 202 in only an orientation that results in both first activation pad 210-A and second activation pad 210-B electrically contacting electrical conductor 230 upon CGM transmitter 200 being fully received in CGM package 202. In other embodiments, CGM package 202 may be of other suitable shapes, construction, and materials, provided that CGM transmitter 200 is configured to be received and enclosed therein such that first activation pad 210-A and second activation pad 210-B each electrically contact an electrical conductor positioned in the interior of CGM package 202.

Figure 3:
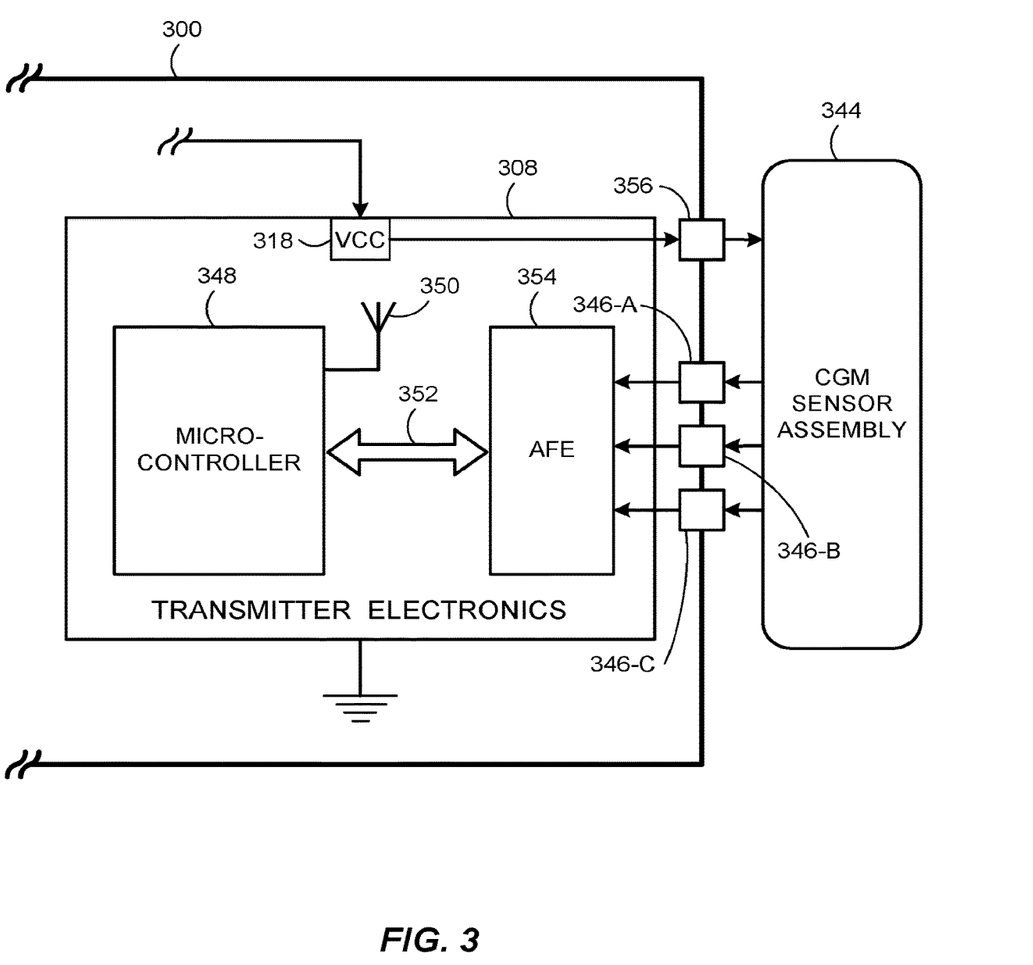
FIG. 3 illustrates a schematic diagram of transmitter electronics of a CGM transmitter coupled to a CGM sensor assembly according to one or more embodiments.

FIG. 3 illustrates wireless transmitter electronics 308 of a CGM transmitter 300 that may be removably coupled to a CGM sensor assembly 344 in accordance with one or more embodiments. Alternatively, in some embodiments, CGM transmitter 300 and CGM sensor assembly 344 may be a single integrated unit. CGM transmitter 300 may be identical or substantially similar to CGM transmitter 100 and/or 200, and transmitter electronics 308 may be identical or substantially similar to transmitter electronics 108. CGM sensor assembly 344 includes sensor electronics and may be configured to obtain glucose readings continually via a sensor component (not shown in FIG. 3; see FIG. 4) inserted in a patient's body. CGM transmitter 300 may include contact pads 346-A, 346-B, and 346-C each configured to electrically contact CGM sensor assembly 344 and receive therefrom glucose readings and to transfer those readings to transmitter electronics 308.

Transmitter electronics 308 may include a power (VCC) input 318, a microcontroller 348, an antenna 350, a serial bus 352, and an analog front end (AFE) circuit 354, and may provide Bluetooth, WiFi, RF, or other suitable wireless communications. Transmitter electronics 308 may provide power to CGM sensor assembly 344 via a power contact 356. Analog front end circuit 354 may process the glucose readings (e.g., provide analog to digital signal conversion) and transfer the converted signals to microcontroller 348 via serial bus 352. Microcontroller 348 may be programmed to further process the converted signals to determine glucose concentrations and transmit via antenna 350 the determined glucose concentrations to a management unit or suitable computer within range of CGM transmitter 300.

Figure 4:
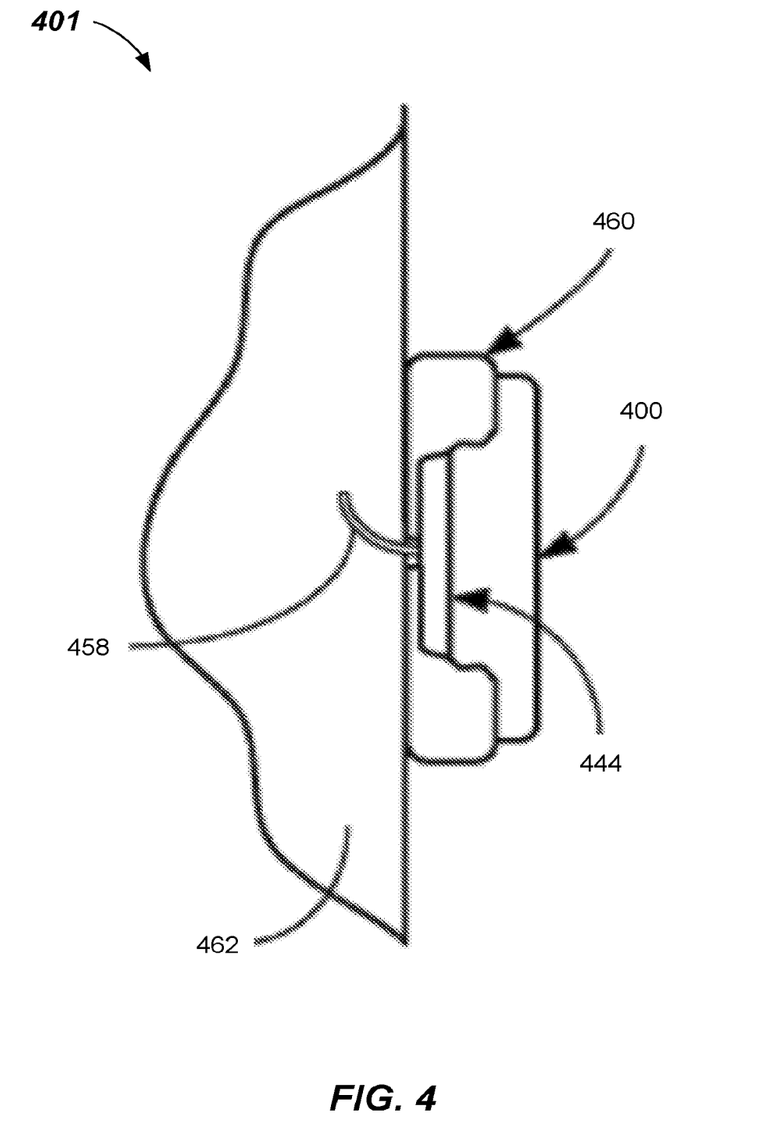
FIG. 4 illustrates a simplified, side view of CGM sensor apparatus according to one or more embodiments.

FIG. 4 illustrates CGM sensor apparatus 401 according to one or more embodiments. CGM sensor apparatus 401 includes a wireless CGM transmitter 400, which may be identical or substantially similar to CGM transmitters 100, 200, and/or 300. CGM sensor apparatus 401 may also include an on-body CGM sensor assembly 444, a sensor component 458, and a sensor pod 460. CGM transmitter 400 may be coupled to on-body CGM sensor assembly 444 in any conventional manner and may provide power to on-body CGM sensor assembly 444 from one or more batteries of CGM transmitter 400. Each of CGM transmitters 100, 200, 300, and/or 400 may be removable from one CGM sensor assembly and reusable with other CGM sensor assemblies. CGM sensor assembly 444 may be identical or substantially similar to CGM sensor assembly 344. Sensor pod 460 may be configured to receive and seat therein CGM sensor assembly 444 and CGM transmitter 400, and may be mountable/attachable to a user's body 462 (e.g., torso) in any conventional manner. Sensor component 458, which may be, e.g., a cannula or needle, may be inserted into the user's body 462 through known means, such as by use of an insertion set. Sensor component 458 may interface with CGM sensor assembly 444 to allow substantially continuous sensing of a blood glucose level in the user's blood. CGM transmitter 400 may communicate sensor readings and other data received from CGM sensor assembly 444 to a CGM management unit or other suitable computer device (neither shown) within range of CGM transmitter 400.

Figure 5:
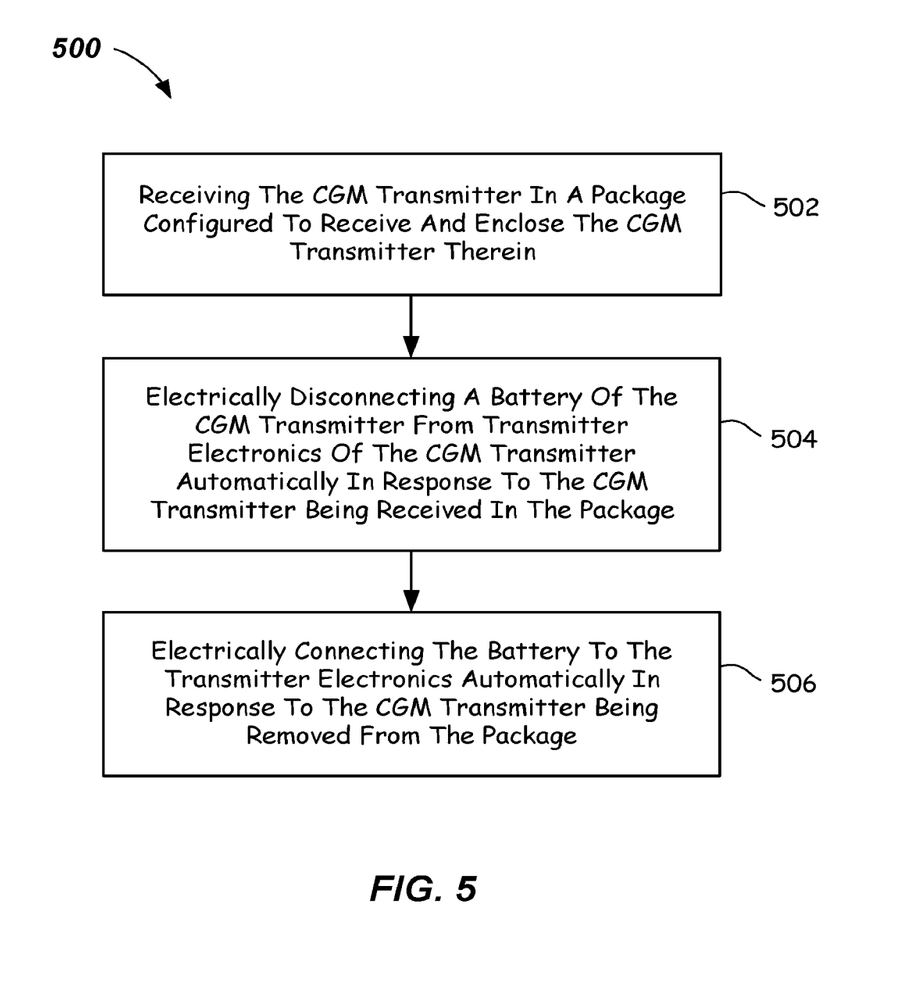
FIG. 5 illustrates a flowchart of a method of reducing battery discharge in a CGM transmitter according to one or more embodiments.

FIG. 5 illustrates a method 500 of reducing battery discharge in a wireless continuous glucose monitoring (CGM) transmitter in accordance with one or more embodiments. Method 500 can be used with, e.g., CGM transmitter 100 and CGM package 102 and/or CGM transmitter 200 and CGM package 202. At process block 502, method 500 can include receiving the CGM transmitter in a package configured to receive and enclose the CGM transmitter therein. For example, as shown in FIGS. 2B-2D, CGM transmitter 200 may be received in CGM package 202, which is configured to receive and enclose therein CGM transmitter 200.

At process block 504, method 500 can include electrically disconnecting a battery of the CGM transmitter from transmitter electronics of the CGM transmitter automatically in response to the CGM transmitter being received in the package. For example, as shown in FIG. 1 and described above, with both first activation pad 110-A and second activation pad 110-B contacting electrical conductor 130, switch disconnect circuit 106 electrically disconnects battery 104 from transmitter electronics 108.

And at process block 506, method 500 can include electrically connecting the battery to the transmitter electronics automatically in response to the CGM transmitter being removed from the package. For example, as also described above in connection with FIG. 1, with second activation pad 110-B electrically floating (e.g., not electrically connected to first activation pad 110-A via electrical conductor 130), switch disconnect circuit 106 electrically connects battery 104 to power input 118 of transmitter electronics 108.

Figure 6:
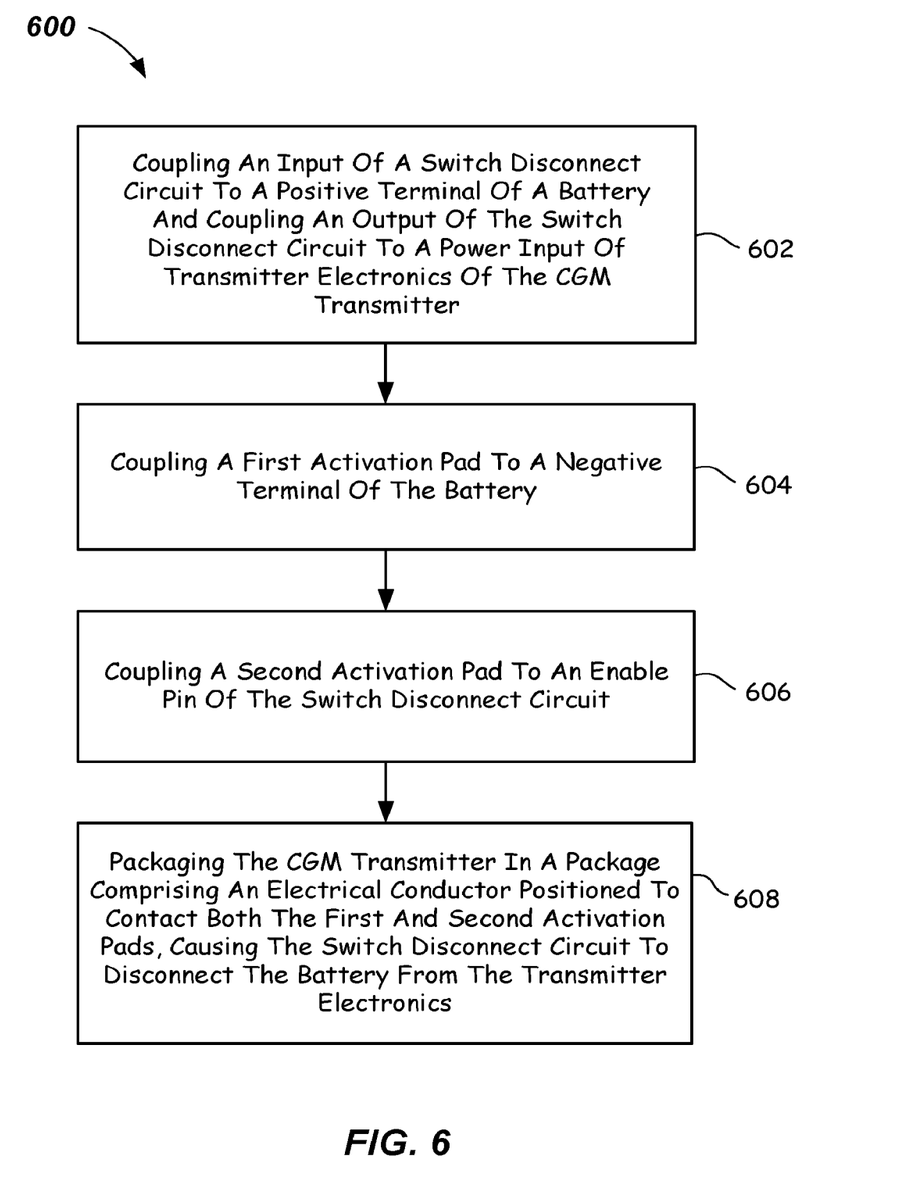
FIG. 6 illustrates a flowchart of another method of reducing battery discharge in a CGM transmitter according to one or more embodiments.

FIG. 6 illustrates a method 600 of reducing battery discharge in a wireless continuous glucose monitoring (CGM) transmitter in accordance with one or more embodiments. Method 600 can be used with, e.g., CGM transmitter 100 and CGM package 102 and/or CGM transmitter 200 and CGM package 202. At process block 602, method 600 can include coupling an input of a switch disconnect circuit to a positive terminal of a battery and coupling an output of the switch disconnect circuit to a power input of transmitter electronics of the CGM transmitter. For example, referring to FIG. 1, the battery may be battery 104, the switch disconnect circuit may be switch disconnect circuit 106, and the transmitter electronics may be transmitter electronics 108.

At process block 604, method 600 can include coupling a first activation pad to a negative terminal of the battery. Again referring to FIG. 1, e.g., the first activation pad may be first activation pad 110-A, which may be coupled to the negative ("−") terminal of battery 104.

At process block 606, a second activation pad can be coupled to an enable pin of the switch disconnect circuit. For example, second activation pad 110-B can be coupled to enable pin 116 of switch disconnect circuit 106 of FIG. 1.

At process block 608, method 600 can include packaging the CGM transmitter in a package comprising an electrical conductor positioned to contact both the first and second activation pads, causing the switch disconnect circuit to disconnect the battery from the transmitter electronics. For example, as shown in FIG. 1, CGM transmitter 100 can be packaged in CGM package 102, which comprises an electrical conductor 130 positioned to contact both first activation pad 110-A and second activation pad 110-B, which causes switch disconnect circuit 106 to disconnect battery 104 from transmitter electronics 108.

In some embodiments, method 600 may also include removing the CGM transmitter from the package to automatically activate the CGM transmitter. Removal of the CGM transmitter from its package causes the switch disconnect circuit to connect the battery to the transmitter electronics in response to the electrical conductor in the package no longer electrically connecting together the first and second activation pads. As described above in connection with FIG. 1, with second activation pad 110-B electrically floating (i.e., not electrically connected to first activation pad 110-A, ground, or voltage), transistor switch 120 turns ON, creating a current path between input pin 112 and output pin 114, which connects battery 104 to power input 118 of transmitter electronics 108.

In some embodiments, method 600 may further include providing the package, the package configured to receive and enclose therein the CGM transmitter. For example, as shown in FIGS. 2B-2D, CGM package 202 may be provided, which is configured to receive and enclose therein CGM transmitter 200.

The foregoing description discloses example embodiments of the disclosure. Modifications of the above-disclosed apparatus and methods which fall within the scope of the disclosure should be readily apparent to those of ordinary skill in the art. Accordingly, while the present disclosure has been disclosed in connection with example embodiments, it should be understood that other embodiments may fall within the scope of the disclosure, as defined by the following claims.

What is claimed is:

1. A wireless continuous glucose monitoring (CGM) transmitter, comprising:
    a first activation pad;
    a second activation pad;
    transmitter electronics;
    a battery; and
    a switch disconnect circuit configured to electrically disconnect the battery from the transmitter electronics when the first activation pad is electrically connected to the second activation pad.

2. The CGM transmitter of claim 1, wherein the switch disconnect circuit comprises:
    an input pin coupled to a positive terminal of the battery;
    an output pin coupled to a power input of the transmitter electronics; and
    an enable pin coupled to the second activation pad.

3. The CGM transmitter of claim 2, wherein the switch disconnect circuit further comprises:
    a transistor switch coupled in series between the input pin and the output pin;
    a logic gate having first and second inputs and an output, the output coupled to the transistor switch to control operation of the transistor switch;
    an inverter coupled between the enable pin and the first input of the logic gate;
    a differential amplifier having an inverting input coupled to the input pin, a non-inverting input coupled to the output pin, and an output coupled to the second input of the logic gate; and
    a current source coupled between the input pin and the enable pin.

4. The CGM transmitter of claim 1, further comprising a package configured to receive the CGM transmitter therein, an interior of the package comprising an electrical conductor positioned to electrically connect the first activation pad to the second activation pad when the CGM transmitter is housed within the package, thereby causing the switch disconnect circuit to electrically disconnect the battery from the transmitter electronics when the CGM transmitter placed in the package.

5. The CGM transmitter of claim 4, wherein removing the CGM transmitter from the package electrically disconnects the first activation pad from the second activation pad, causing the switch disconnect circuit to electrically connect the battery to the transmitter electronics.

6. The CGM transmitter of claim 1, further comprising a CGM sensor assembly coupled to the transmitter electronics, the CGM sensor assembly comprising sensor electronics configured to continually measure a concentration of glucose in a body fluid via a sensor component.

7. The CGM transmitter of claim 6, wherein the CGM transmitter is removably coupled to the CGM sensor assembly.

8. The CGM transmitter of claim 1, wherein the transmitter electronics comprises:
    a microcontroller;
    an antenna coupled to the microcontroller;
    an analog front end circuit configured to be coupled to a sensor assembly for sensing an analyte in a bodily fluid; and
    a serial bus coupling the analog front end circuit to the microcontroller.

9. A method of reducing battery discharge in a wireless continuous glucose monitoring (CGM) transmitter, the method comprising:
    electrically disconnecting a battery of the CGM transmitter from transmitter electronics of the CGM transmitter by placing the CGM transmitter into a package that electrically connects a first activation pad with a second activation pad of the CGM transmitter; and
    electrically connecting the battery to the transmitter electronics when the CGM transmitter is removed from the package.

10. The method of claim 9, wherein electrically connecting the battery comprises removing the CGM transmitter from the package to electrically disconnect the first activation pad from the second activation pad.

11. The method of claim 9, wherein the CGM transmitter comprises a switch disconnect circuit having an input pin coupled to a positive terminal of the battery, an output pin coupled to a power input of the transmitter electronics, and an enable pin coupled to the second activation pad; and wherein the switch disconnect circuit electrically disconnects the battery from the transmitter electronics in response to an electrical connection of the first activation pad to the second activation pad.

12. A battery-operated electronic device, comprising:
    a first activation pad;
    a second activation pad;
    device electronics;
    a battery; and
    a switch disconnect circuit configured to electrically disconnect the battery from the device electronics when the first activation pad is electrically connected to the second activation pad.

13. The battery-operated electronic device of claim 12, further comprising a package configured to receive the battery-operated electronic device, an interior of the package comprising an electrical conductor positioned to electrically connect the first activation pad to the second activation pad when the battery-operated electronic device is housed within the package, thereby causing the switch disconnect circuit to electrically disconnect the battery from the device electronics when the battery-operated electronic device is received within the package.

14. The battery-operated electronic device of claim 13, wherein removing the battery-operated electronic device from the package electrically disconnects the first activation pad from the second activation pad, causing the switch disconnect circuit to electrically connect, causing the switch disconnect circuit to electrically connect the battery to the device electronics.

15. The battery-operated electronic device of claim 12, wherein the device electronics comprises:
    a microcontroller;
    an antenna coupled to the microcontroller;

an analog front end circuit configured to be coupled to a sensor assembly for sensing an analyte in a bodily fluid; and a serial bus coupling the analog front end circuit to the microcontroller.

16. The battery-operated electronic device of claim 12, wherein the switch disconnect circuit comprises:

an input pin coupled to a positive terminal of the battery;

an output pin coupled to a power input of the device electronics; and an enable pin coupled to the second activation pad.

17. The battery-operated electronic device of claim 16, wherein the switch disconnect circuit comprises:

a transistor switch coupled in series between the input pin and the output pin;

a logic gate having a first input, a second input, and an output,
wherein the output is coupled to the transistor switch to control operation of the transistor switch;

an inverter coupled between the enable pin and the first input to the logic gate;

a comparator having a first input coupled to the input pin, a second input coupled to the output pin, and an output coupled to the second input of the logic gate; and a current source coupled between the input pin and the enable pin.

18. A method of reducing battery discharge in a battery-operated electronic device, the method comprising:

coupling an input of a switch disconnect circuit within the battery-operated electronic device to a positive terminal of a battery and coupling an output of the switch disconnect circuit to a power input of device electronics of the battery-operated electronic device;

coupling a first activation pad of the battery-operated electronic device to a negative terminal of the battery;

coupling a second activation pad of the battery-operated electronic device to an enable pin of the switch disconnect circuit; and packaging the battery-operated electronic device in a package having an electrical conductor within an interior of the package, the electrical conductor positioned to electrically connect the first activation pad to the second activation pad, thereby electrically disconnecting the battery from the device electronics of the battery-operated electronic device.

19. The method of claim 18, further comprising removing the battery-operated electronic device from the package to electrically disconnect the first activation pad from the second activation pad, thereby causing the switch disconnect circuit to connect the battery to the device electronics.

20. The method of claim 18, wherein the package comprises a front, a back, a top, a bottom, and side panels configured to receive and enclose the battery-operated electronic device therein.

* * * * *